(12) United States Patent
Garms, III

(10) Patent No.: US 6,597,761 B1
(45) Date of Patent: Jul. 22, 2003

(54) LOG EVALUATION USING CYLINDRICAL PROJECTIONS

(75) Inventor: Walter I. Garms, III, Palo Alto, CA (US)

(73) Assignee: InVision Technologies, Inc., Newark, CA (US)

(*) Notice: Subject to any disclaimer, the term of this patent is extended or adjusted under 35 U.S.C. 154(b) by 132 days.

(21) Appl. No.: 09/792,650

(22) Filed: Feb. 23, 2001

(51) Int. Cl.⁷ ............................................... G01N 23/02
(52) U.S. Cl. ............................. 378/58; 378/4; 382/154; 702/35; 702/40
(58) Field of Search ................................ 378/4, 58, 901; 702/35, 40; 382/154

(56) References Cited

U.S. PATENT DOCUMENTS

| | | | |
|---|---|---|---|
| 4,135,247 A | 1/1979 | Gordon et al. | 364/414 |
| 4,283,629 A | 8/1981 | Habermehl et al. | 250/445 |
| 4,879,752 A | 11/1989 | Aune et al. | 382/1 |
| 4,916,629 A | * 4/1990 | Bogue et al. | 702/40 |
| 5,023,805 A | 6/1991 | Aune et al. | 364/507 |
| 5,257,101 A | 10/1993 | Lee | 358/101 |
| 5,262,956 A | 11/1993 | DeLeeuw | 364/474.13 |
| 5,394,342 A | 2/1995 | Poon | 364/558 |
| 5,412,220 A | 5/1995 | Moore | 250/563 |
| 5,765,617 A | 6/1998 | Mierau et al. | 144/387 |
| 5,920,317 A | 7/1999 | McDonald | 345/356 |
| 5,960,104 A | 9/1999 | Conners et al. | 382/141 |
| 6,026,376 A | 2/2000 | Kenney | 705/27 |
| 6,151,379 A | 11/2000 | Kullenberg et al. | 378/54 |
| 6,157,698 A | 12/2000 | Pietikainen et al. | 378/58 |
| 6,217,214 B1 | 4/2001 | Cabral et al. | 378/196 |
| 6,229,872 B1 | * 5/2001 | Amos | 378/58 |
| 6,353,445 B1 | 3/2002 | Babula et al. | 345/733 |

OTHER PUBLICATIONS

Skatter, S., "Determination of Cross–Sectional Shape Of Softwood Logs From Three X–Ray Projections Using An Elliptical Model" Holz als Roh– und Werkstoff 56 (1998) 179–186. ©Springer–Verlag 1998.

"CT Imaging, Data Reduction, and Visualization of Hardwood Logs" by Daniel L. Schmoldt, pp. 69–80, Hardwood Symposium Proceedings, May 8–11, 1996.

"Nondestructive Evaluation of Hardwood Logs: CT Scanning, Machine Vision and Data Utilization" by Daniel L. Schmoldt, Luid G. Occena, A. Lynn Abbott, and Nand K. Gupta, pp. 279–309, Nondestructive Testing Evaluation, vol. 15, ©1999 Overseas Publishers Association N.V. Received Aug. 20, 1998.

* cited by examiner

Primary Examiner—Drew A. Dunn
Assistant Examiner—Allen C. Ho
(74) Attorney, Agent, or Firm—Bever, Hoffman & Harms, LLP; James E. Parsons

(57) ABSTRACT

A three-dimensional density distribution of a log is reduced to a two-dimensional structure that provides a convenient image or visualization of defects like knots or voids in a log, to facilitate grading and/or optimization of a sawing strategy for the log. The two-dimensional data structure is based on cylindrical or modified cylindrical coordinates Z and θ. To provide a more compact identification of defects, modified cylindrical coordinates use a Z-axis that follows the growth center in the log and determines data points by evaluating properties of the log along rays at an upward angle corresponding to limbs in a tree. A process for identifying the growth center at any distance Z along the length of the log examines or accumulates the gradient of density along lines through a cross-section of the log. Manual grading and sawing optimization can employ viewing of an image based on the two-dimensional data structure with superimposed marks indicating the boundaries of faces cut from the log. Automated grading and sawing optimization employs the two-dimensional data structure to reduce processing time when compared to processes that manipulate three-dimensional data structures.

32 Claims, 12 Drawing Sheets

LOG EVALUATION USING CYLINDRICAL PROJECTIONS

COPYRIGHT NOTICE

A portion of the disclosure of this patent document contains material which is subject to copyright protection. The copyright owner has no objection to the facsimile reproduction by anyone of the patent document or the patent disclosure, as it appears in the Patent and Trademark Office patent files or records, but otherwise reserves all copyright rights whatsoever.

REFERENCE TO APPENDIX ON COMPACT DISC

An Appendix containing a computer program listing is submitted on a compact disc, which is incorporated by reference herein in its entirety. The total number of compact discs including duplicates is two. Each of the compact discs includes a file named "RadialImageCode.txt", which was created Jan. 26, 2001 and has a size of 44,826 bytes.

BACKGROUND

Logs are non-standard commodities that contain defects such as knots and cracks that significantly affect the value of boards cut from the log. Accordingly, when buying logs, a grader evaluates each log to determine the extent and locations of defects in the log. A sawyer, when cutting the log, attempts to select a sawing strategy that provides the highest value for the lumber cut from the log. These graders and sawyers typically depend on the external appearance of a log when grading or evaluating the log, but viewing the exterior of a log gives the grader or sawyer an imprecise indication of the quality of a log and often fails to indicate internal defects. This results in economic inefficiency because logs are inaccurately graded or cut.

Log scanning devices have been developed to improve the evaluation of logs and the optimization of sawing strategies. For example, U.S. Pat. No. 5,394,342 describes a scanning system that applies circumferentially spaced traverse scans along the length of a log to provide longitudinal density data. A paper by D. Schmoldt, entitled "CT Imaging, Data Reduction, and Visualization of Hardwood Logs," Hardwood Symposium Proceedings, (May 1996) and a paper D. Schmoldt et al entitled "Nondestructive Evaluation of Hardwood Logs: CT Scanning, Machine Vision and Data Utilization," Nondestr. Test Eval., Vol. 15 (1999) describe CT (computer tomography) scanning of logs and evaluation of data resulting from CT scanning of a log.

The three-dimensional data structures and the large amount of data that scanners generate for a log are often difficult to use. For example, data indicating a three-dimensional density distribution for a log is difficult for a grader or sawyer to visualize, and computer manipulation of the large amount of data requires significant processing power or time. Efforts are continuing to improve the methods for quantifying the properties of logs, visualizing the data associated with the logs, and optimizing log grading and sawing strategies based on such data.

SUMMARY

In accordance with an aspect of the invention, a three-dimensional density distribution for a log is processed to provide a convenient image or visualization of defects like knots or voids in a log and thereby facilitate grading and optimization of a sawing strategy for a log. The data representing such images has a two-dimensional structure and contains considerably less data than a three-dimensional density distribution. Accordingly, manipulation of data structures in accordance with the invention requires less processing power or time in automated processes for grading or optimization of a sawing strategy. Other aspects of the invention provide processes for grading and optimizing the sawing strategies based on the two-dimensional data structures.

In one embodiment, a visualization of a log provides a two-dimensional image where intensities (or colors) in the image correspond to a property evaluated along at least portions of cylindrical projections extending from the center of the log. Exemplary properties shown in the image include but are not limited to the average density along a projection, a minimum or maximum density along a projection, existence of a steep change in density along a projection, and flags indicating the presence or absence of defects along a projection. A central axis from which the projections extend can be straight or can follow the center of growth rings in the log, and the projections can be perpendicular to the axis or extend at an upward angle characteristic of the branches in a tree. A viewer of this image can quickly identify an orientation for the log that presents the fewest defects to a first cut of a saw blade.

One exemplary embodiment of the invention is a data structure for describing a log. The data structure includes a two-dimensional array of data values. Each data value corresponds to values of a coordinate Z and a second coordinate $\theta$. The coordinate Z indicates distance along the log, and the coordinate $\theta$ indicates an angle around the log. Each data value indicates a property of the log that is evaluated along a ray that originates at a center point corresponding to the value of the coordinate value Z and extends in a direction corresponding to the coordinate value $\theta$. The center point at each value of the coordinate Z is typically the growth center of the log at that Z-coordinate value but alternatively can be the geometric center of the log or of core wood in the log. The ray evaluated to determine a data value can be perpendicular to the length of the log or directed at an upward angle along the log. The upward angle typically depends on a growth direction characteristic of tree limbs in the species of tree that produced the log or is determined independently for each log. Optionally, each data value indicates a property of the log that is evaluated in a range of distances along the ray that originates at the center point. The range can be limited to exclude core wood in the center of log and or bark on the outside of the log. In one specific embodiment, each data value indicates presence or absence of a defect corresponding to the coordinates of the data value and may further indicate the depth or location along the ray for any defect on the ray.

Another embodiment of the invention is a method for generating a description of a log. For a set of locations along the length of the log, the method finds a center point (e.g., a geometric or growth center) of the log. Each ray in a set of rays that extend from the center points is evaluated. In particular, the method evaluates a property of the log along each ray to generate a data value corresponding to Z and $\theta$ coordinates identifying the direction of the ray. Typically, the evaluated property is density along the ray, and the evaluation determines whether there is a defect along the ray. A CT scan of the log can generate a three-dimensional data structure that provides the densities evaluated along the rays. A two-dimensional data structure that describes the log includes the data values, which are positioned in the two-dimensional data structure according to their respective coordinates.

Another embodiment of the invention is a system for evaluating logs. The system includes program code that is computer executable for manipulating a data structure such as described in the preceding paragraph. Generally, the system further includes a display device and a processor capable of executing the program code. In executing the program code, the processor controls display of an image on the display device. The image includes pixels that correspond to the data values of the data structure and have shades defined by the respective data values. The system can further superimpose marks on the image to indicate boundaries of one or more faces of the log that results from sawing the log. The marks can be shifted relative to the image identify an optimal orientation for sawing the log that minimizes the defects present between the boundary marks, i.e., in the cut faces of the log.

Another embodiment of the invention is method for grading a log. The grading method uses a two-dimensional defect structure or data array as described above that includes data values indexed by cylindrical or modified cylindrical coordinates. The grading method evaluates the two-dimensional array to determine sizes of blocks that are free of data values indicating defects. Each defect-free block contributes to a grade value of the log, according to the size of the block. Evaluation of the two-dimensional array can be performed manually, e.g., by a grader viewing an image having pixels shaded according to corresponding data values. The grader easily and quickly recognizes the sizes of the blocks through evaluating areas of the image having a shade indicating an absence of defects, and the grader can assign the grade to the log based on the viewing of the image. To aid the grader, superimposed marks in the image indicate boundaries of one or more board faces that results from a sawing strategy for the log, and the grader can shift the image relative to the marks to minimizes defects within the one or more board faces. The manual process can also select an orientation for sawing of the log according to positions of the marks that minimize defects in the board faces.

The grading process can also be automated through a computer program that manipulates the two-dimensional array. One exemplary computer program includes: (a) determining a number N of data values that are consecutive in a direction of the coordinate $\theta$ and correspond to a desired width of defect-free wood; (b) scanning the two-dimensional array in the direction of the coordinate $\theta$ until identifying N consecutive data values that indicate absence of a defect; (c) scanning the two-dimensional array in a direction of the coordinate Z to determine a size of a block that is defect free; (d) increasing the grade value for the log by an amount corresponding to the size of the defect-free block; (e) repeating steps (b), (c), and (d) to account for all defect-free blocks in the two-dimensional data structure.

Another embodiment of the invention is an automated grading process that accounts for the sawing strategy and the optimal log orientation for the sawing strategy. An exemplary embodiment of this grading method includes: (a) creating a two-dimensional data or defect structure of a type described above; (b) selecting a sawing strategy for the log; (c) selecting an orientation of the log for the sawing strategy; (d) identifying a sub-array of the two-dimensional array, the sub-array corresponding to a face of the log resulting from the sawing strategy and the orientation; (e) evaluating the sub-array to determine sizes of blocks in the sub-array, that are free of data values indicating defects; (f) assigning a first grade value to the face according to the block sizes; (g) repeating steps (d), (e), and (f) for one or more faces of the log resulting from the sawing strategy and the orientation; (h) combining the grade values of the faces to generate a grade value for the orientation; and (i) repeating steps (c) to (h) for one or more additional orientations of the log; (j) assigning a grade value to the log based on a best of the grade values for the orientations.

Yet another embodiment of the invention is method for identifying a growth center of a log. The method determines an accumulated absolute value of a gradient of the density, or the number of zero crossings of the gradient, along lines through a cross-section of the log and identifies two crossing lines that have the largest accumulated values or the greatest numbers of zero crossings. The growth center is at the intersection of the crossing lines. Generally two sets of lines are considered, wherein the lines in the first set are perpendicular to the lines in the second set. To reduce the number of lines evaluated, the method can determine a geometric center of the log and select a small central area containing the geometric center of the log. The lines evaluated are limited to those passing through the central area. In accordance with a further aspect of the invention, considering only densities for points inside the central area when determining the accumulated absolute values of the gradient of the density reduces the complexity of the calculation.

These and other embodiments of the invention will be better understood in light of the detailed description below when taken with the accompanying drawings.

BRIEF DESCRIPTION OF THE DRAWINGS

Use of the same reference symbols in different figures indicates similar or identical items.

DETAILED DESCRIPTION

In accordance with an aspect of the invention, a process for grading logs and optimizing sawing strategies for logs is based on computer tomography data and modified cylindrical projections used to represent the log in two-dimensional images and data structures. This two-dimensional representation facilitates defect identification, dramatically reduces the amount of data required to describe the defect structure of a log, and allows a person or a computer to quickly and efficiently grade a log or optimize a sawing strategy for the log.

Computer tomography (CT) scanning generally provides a three-dimensional data structure. Each value in the data structure corresponds to a small volume (or voxel) and indicates a density or an absorption coefficient for the voxel. Each voxel further has three Cartesian coordinates Xc, Yc, and Zc that indicate the relative locations of the voxels. Known CT scanners can analyze logs and provide three-dimensional data structures representing logs. In an exemplary embodiment of the invention, a CT scanner system such as described in co-filed U.S. Pat. app. Ser. No. 09/891,734 (Attorney Docket number M-8684 US) provides the three-dimensional data structures for a log. The amount of data in a three-dimensional data structure depends on the size of the log and resolution required for useful evaluation of the log. Depending on the resolution, a single 4-meter log, for example, might require 800 MB of data in the standard three-dimensional format. This amount of data is time consuming to process. Additionally, the three-dimensional nature of the data makes the data difficult to visualize, store, or transmit.

Figure 1:
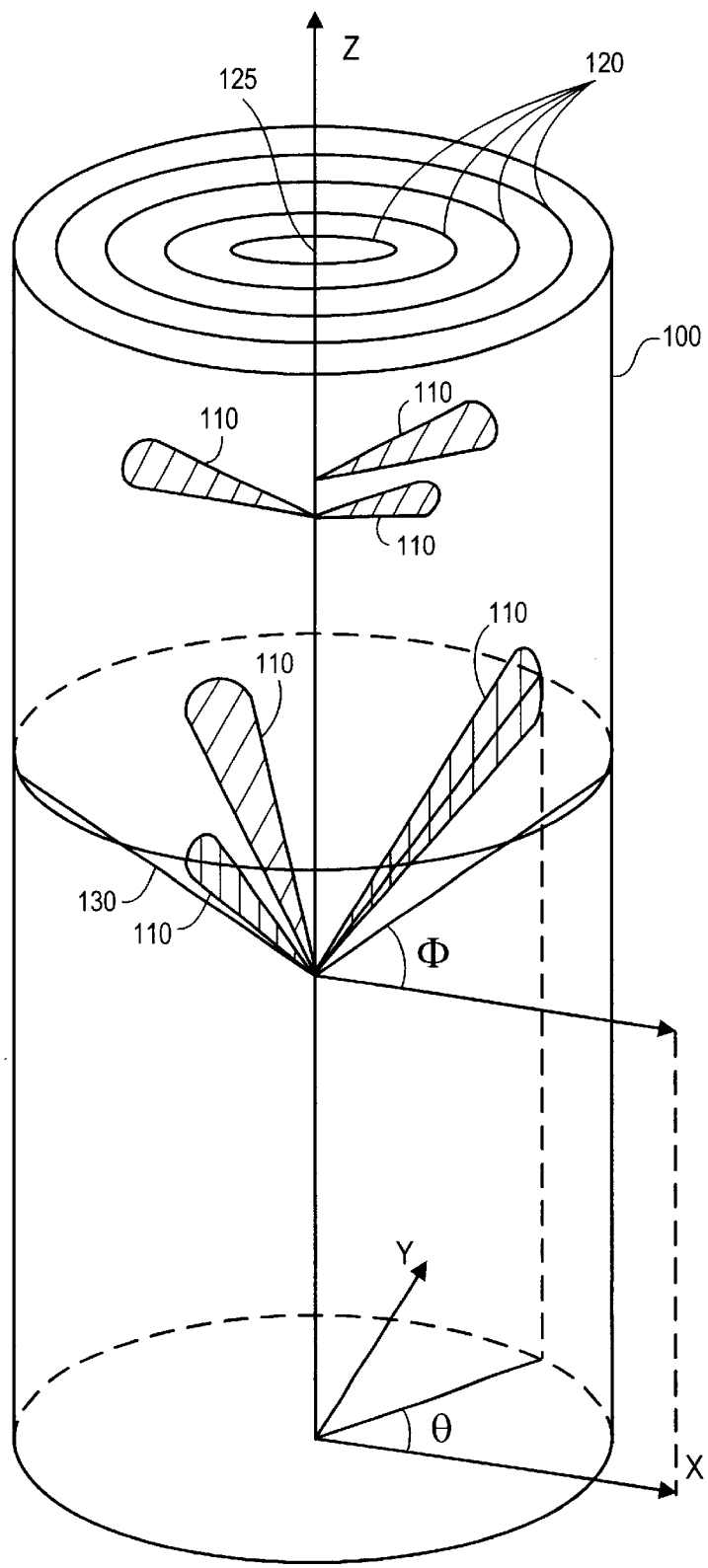
FIG. 1 illustrates Cartesian and modified cylindrical representations of a log.

In accordance with an aspect of the invention, a representation of the defects or other structures in a log uses a modified cylindrical coordinate system. FIG. 1 illustrates a log 100 and a Cartesian coordinate system defining coordinates Xc, Yc, and Zc for each point or voxel in the log. The Zc coordinate represents the distance along the length of the log (up, in a standing tree), and the Xc and Yc coordinates define a location in planes perpendicular to the Zc-axis. A set of CT cross sectional images taken at intervals along the length of the log provide data points (e.g., density values) corresponding to Xc-Yc planes at discrete values of the Zc coordinate. As mentioned above, this three-dimensional system can include a large amount of data, making any sort of optimization and grading process complex and time consuming.

One of the most important aspects of tree structure and the defect structure in a log is the center 125 of the annual growth rings 120. Generally, the center 125 of the annual rings 120, sometimes referred to herein as growth center 125 can be a significant distance from the geometric center of a cross-section of a tree or log, and the position of growth center 125 changes, albeit slowly, with the Zc coordinate. Most significant cracks in a typical log pass through the center of the growth rings (e.g., growth center 125). Knots 110, which are the portions of tree limbs in the tree trunk or log, generally extend upward and radially away from growth center 125. Imbedded knots, which commonly result when the lower branches of a tree break off and the tree grows clear wood over the previous location of the branch, also extend upward and radially away from growth center 125. Imbedded knots may leave little or no visible signs on the surface of a log, but knowledge of the existence and extent of imbedded knots is critical to the sawyer or log grader.

In accordance with an aspect of the invention, an efficient two-dimensional representation or image of the defects in the logs arises from basic knowledge of the structures of trees and defect in logs. The two-dimensional image can be described as a Z-θ plot of a log's properties and is created using a cylindrical projection of the known defects. In the image, each point corresponds to coordinates (Z,θ) that uniquely identify a ray, and the grayscale (or color) value at the point in the image depends on some scalar value evaluated for the corresponding ray.

For a conventional cylindrical coordinate system, the Z-axis is a straight line, and each value of coordinate Z defines an X-Y plane. The θ coordinate is an angle identifying a projection of a ray in the X-Y plane. In accordance with one embodiment of the invention, a modified cylindrical coordinate system has a Z axis that follows the center 125 of the growth rings 120 and accordingly bends as the position of growth center 125 changes from one value of Z to the next. For a further modification of the cylindrical coordinate system, each value of coordinate Z identifies a cone (e.g., cone 130) extending at an upward angle Φ. For angle Φ equal to zero, the cone is actually a plane as in a conventional cylindrical coordinate system. The upward angle Φ typically depends on the log or the species of tree that provided the log. For example, different trees or species of trees have limbs that grow at different characteristic angles with horizontal. For example, a pine tree may have limbs that grow nearly horizontal from the trunk of the tree, while hardwood trees have limbs with a distinct upward angle. Angle Φ can be selected according to the species of the log or according to evaluation of a particular log. With the modified cylindrical coordinates, each value of coordinate Z identifies a plane or cone, and each value of coordinate θ identifies a ray in the plane or cone.

A two-dimensional data structure according to an embodiment of the invention and an image generated from the two-dimensional data array represents a set of values identifying properties of a log along rays corresponding to particular coordinate values Z and θ in the modified cylindrical coordinate system. A value in the data structure can be but is not limited to the average density over all or a portion of the associated ray, the severity of any defect on the ray, the distance from the center 125 or outside edge of log 100 to the defect, and similar measures of "good" wood, as opposed to defects. In accordance with another aspect of the invention, an embodiment of a data structure or image only includes features determined to be defects.

There are several ways to form images or data structures in accordance with the invention. One method determines the positions of defects using Cartesian coordinates Xc, Yc, and Zc and coverts those coordinates to the Z-θ space. Another method directly evaluates a desired property or scalar value along each ray corresponding to a Z-θ value.

Figure 2:
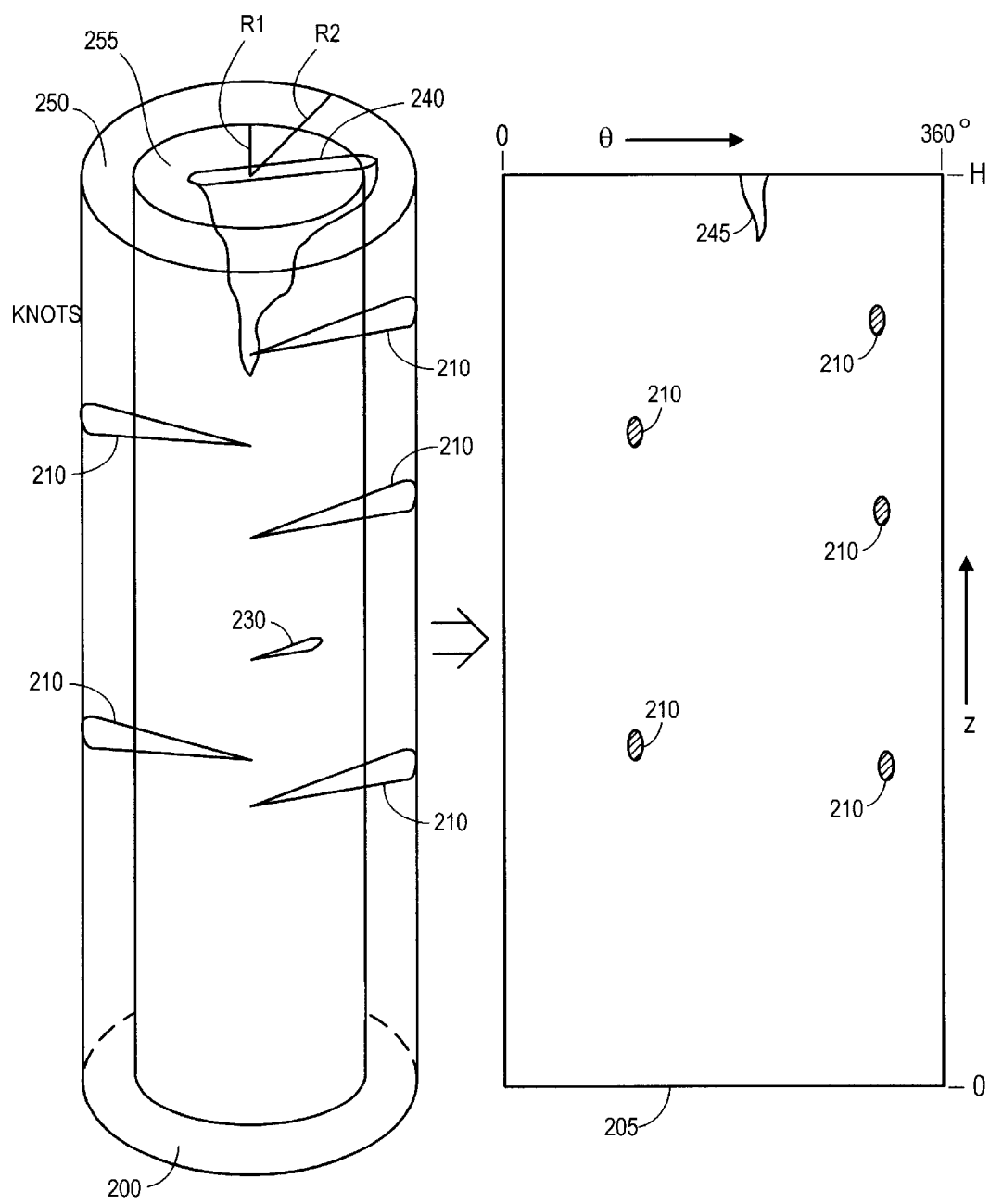
FIG. 2 illustrates a relationship between a portion of a log and an image or defect structure of the log in accordance with and embodiment of the invention.

FIG. 2 illustrates the relation between a log 200 and a data structure or image 205. In many cases the sawyer or log grader is not interested in the core of the log, and as is not interested in the structure of the bark on the log. Image 205 corresponds to an annular cylinder 250 having an inner limit R1 and an outer limit R2. Inner limit R1 is chosen to exclude less valuable core wood 255 from image 205. Outer limit R2 can be chosen to exclude bark and/or sapwood. Typically, outer limit R2 is at a set distance from the outside edge of the log so that the annular cylinder is not circular and has a varying thickness depending of the shape of the log. Alternatively, outer limit R2 can be a radius of fixed length. The property represented in image 205 is thus limited to a particular range of distances or percentages of the radius to ignore defects that are either too close to the center, or too close to the outside edge of the log. When the evaluated portions of the rays are limited, the Z-θ image 205 as illustrated in FIG. 2 can be roughly thought of as a tubular portion of log 200 that is unrolled and laid flat. This representation of tree structure is extremely efficient, reducing the volume of data from three dimensions to two and selecting the critical data. This simplifies manual or automated grading of the log and simplifies the optimization of a sawing or selecting a veneering pattern for log 200.

In general, analysis of the CT density data of log 200 indicates the presence of two types of defects, low-density and high-density. A low-density defect typically corresponds to a crack 240 or a void area (not shown) in log 200. A high-density defect typically corresponds to a knot 210. The defects 210 and 240 appear in defect structure 205 and can be represented using different colors or grayscale levels, e.g., light shade or white for low density defects, a medium shade for no defects, and a dark shade for high density defects. A nearly unlimited number of variations for such images are possible based on the same underlying data structure.

The selection R1 and R2 limits image 205 to showing only the defects in the best wood 250. For example, crack 240 is predominantly in core wood 255 so that only a relatively small defect 245 appears in defect structure 205. A projection through the entire log onto a plane or a full radial projection would show a much larger defect area associated with crack 240. Further, radial projections of crack 240 from the geometric center of log 200 rather than from the growth center would spread the representation of crack 240 over a larger angular range since typical cracks pass through the growth center. An imbedded knot 230, which is in core wood 255 but does not extend to inner radius R1, would appear in a projection onto a plane or a complete radial projection. Image 205 does not include imbedded knot 230 because knot 230 does not extend into the region 250 of interest. Accordingly, the data structure and image 205 indicates the defects actually in the wood of interest in a manner that is precise and easy to interpret. A sawing strategy based on defect structure 205 can more easily provide a best sawing strategy for sawing the best wood 250 in log 200.

Figure 3A:
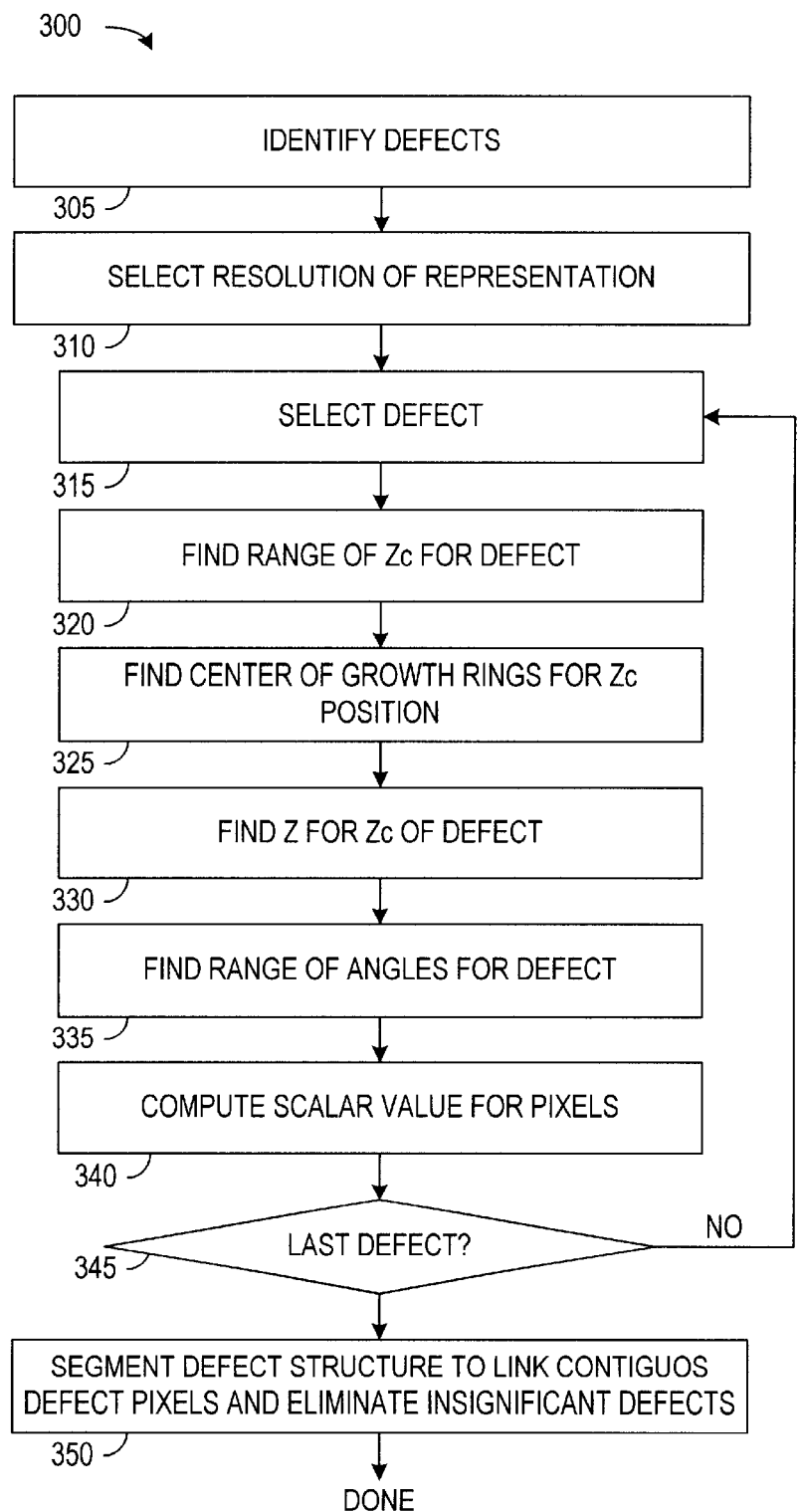
FIG. 3A is a flow diagram of a process for determining a defect structure of a log.

FIG. 3A is a flow diagram of a process 300 for generating a two-dimensional defect or data structure for a Z-θ image (e.g., image 205) from the CT data given in a three-dimensional Cartesian coordinate system Xc, Yc, and Zc. An initial step 305 identifies defects in the three-dimensional data structure using known processing techniques or the techniques described further below. The next step 310 selects the size or resolution of the Z-θ image. For example, if a pixel in the Z-θ image represents one centimeter in the Z direction and one degree of angle, the resulting image for a 4-meter log would then be 400 pixels high and 360 pixels wide (assuming the Z axis is vertical). A data structure accommodating the selected resolution of size is allocated for the image, and all points in the data structure are set to zero or a value representing a background color.

Step 315 selects one of the defects identified in step 305. Steps 320, 325, 330, 335, and 340 then calculate image data or pixel values for the selected defects. More particularly, step 320 determines the range of values of Cartesian coordinate Zc corresponding to the selected defect (i.e., the Zc size or height of the defect) which will be converted into a range of values for the modified cylindrical coordinate Z. For process 300, the modified cylindrical coordinates employ rays originating from the grow center of the log. Alternatively, process 300 could use coordinates with a straight Z-axis or a Z-axis that follows the geometric center of the log or heartwood in the log.

Figure 3B:
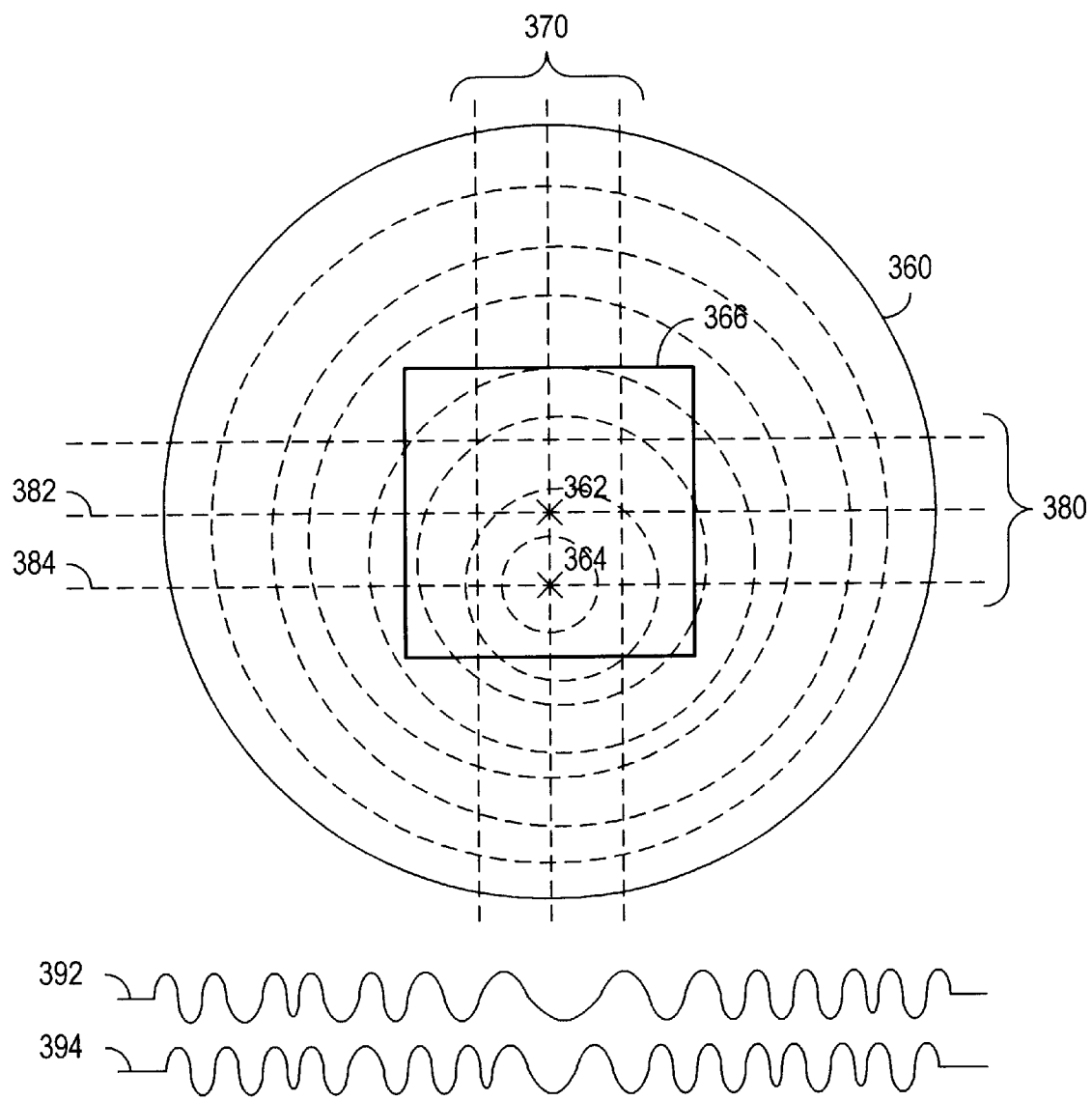
FIG. 3B is illustrates density variations in a cross-section of a log as used to identify the center of growth rings in the log.

Step 325 determines the position of the center of the annual growth rings at that Zc coordinates of the defect. FIG. 3B illustrates one method for finding the growth center. The method processes the density data for a cross-section 360 of the log to identify horizontal and vertical lines that cross the greatest number of annual rings. This method finds the approximate location of the geometric center 362 of cross-section 360 using conventional means and then selects a central area 366 around geometric center 362. In FIG. 3B, central area 366 is a square or rectangle. The growth center 364 is likely to be within central area 366 if central area 366 is appropriately sized for the species and diameter of the log.

Vertical lines 370 and horizontal lines 380 crossing central area 366 correspond to columns and rows of densities in the density array representing cross-section 360. The growth center can be identified from the sum of the absolute value of the gradient of the density or from the number of zero crossings of the density gradient. For each of lines 370 and 380, the sum of absolute values of the gradients (e.g., the sum of absolute differences in densities of adjacent voxels) depends on the number of times the density crosses the average density on that line. The sum of the absolute value or zero crossings of the density gradient can be determined for the entire length of the line or just for the portion of the line within central area 366.

Density plots 392 and 394 indicate the variation in density along lines 382 and 384 respectively. The horizontal line 384 with the highest sum of gradients or the most zero crossings in the density gradient crosses growth center 364, and indicates the Yc position of growth center 364. A more accurate determination of the Yc position of growth center 364 can be obtained by fitting the summed gradients for horizontal lines 380 to a curve and finding the peak of the curve. The process is repeated for vertical lines 370 summing absolute gradients (i.e., summing the absolute differences between densities of adjacent voxels in a column) or counting zero crossings in the density gradient to find the Xc position of growth center 364.

For some values of coordinate Zc, the determined Xc and Yc positions for the growth center 364 may be unreliable, especially if the corresponding slice of the log crosses several knots. For example, the determined Xc and Yc positions may be unreliable if there is no obvious peak in the x or y gradient data, or the detected center is at the edge of central area 366. The determined Xc and Yc positions may also be determined to be unreliable if the detected position differs significantly from the result of the neighboring values of coordinate Zc. If the determined Xc and Yc positions appear to be unreliable, the central area 366 can be expanded to widen the search for growth center 364. If the Xc and Yc positions are still unreliable, the reliable growth center coordinates for the various cross-sections of the log can be fit to a curve or combined in a local average (excluding or including the unreliable points). For most values of coordinate Zc, the calculation of Xc and Yc positions provides reliable results, and generally, the center of growth rings does not change quickly. Accordingly, if the determined Xc and Yc for one Zc value is determined to be unreliable (e.g., differ significantly from the average of the neighboring values of Zc), we can interpolate fit curve or use the local average to provide reliable growth center coordinate Xc and Yc.

Returning to FIG. 3A, when the surface corresponding to constant Z coordinate is a cone, the Z and Zc coordinates differ depending on the distance between the defect and the growth center. In particular, if Zc and R are the normal cylindrical coordinates with Zc-axis through the appropriate growth center, Z is less than Zc by $R*\tan((\Phi))$ for an upward limb angle $\Phi$ as shown in FIG. 1. Step 330 calculates the range of coordinate Z for the selected defect assuming a constant position of the center of the growth rings, which is largely correct over the size of a typical defect such as a knot. Step 335 calculates the range of angle θ for the defect again using the identified center of the growth rings. Once the ranges for Z and θ are known, step 340 computes a scalar value for each (Z,θ) in the ranges. The scalar value ideally indicates the severity, depth, or type of the defect in a trajectory associated with the Z-θ coordinates. The trajectory can be a ray extending from the origin (e.g., the center of the growth rings) or may only extend between particular radii (e.g., R1 and R2 in FIG. 2). The determined scalar values are stored in the two-dimensional data structure associated with the Z-θ image.

Step 345 determines whether the last of the identified defect has been handled. If not, process 300 branches back to select another of the defects. After processing the last defect, defect areas have calculated data values and the non-defect areas have the background values set during initialization of the data structure. Process 300 then continues to a segmentation step 350. Step 350 processes the data or defect structure to link contiguous defect pixels into defect groups and removes groups that do not contain enough pixels to be a significant defect.

Figure 4:
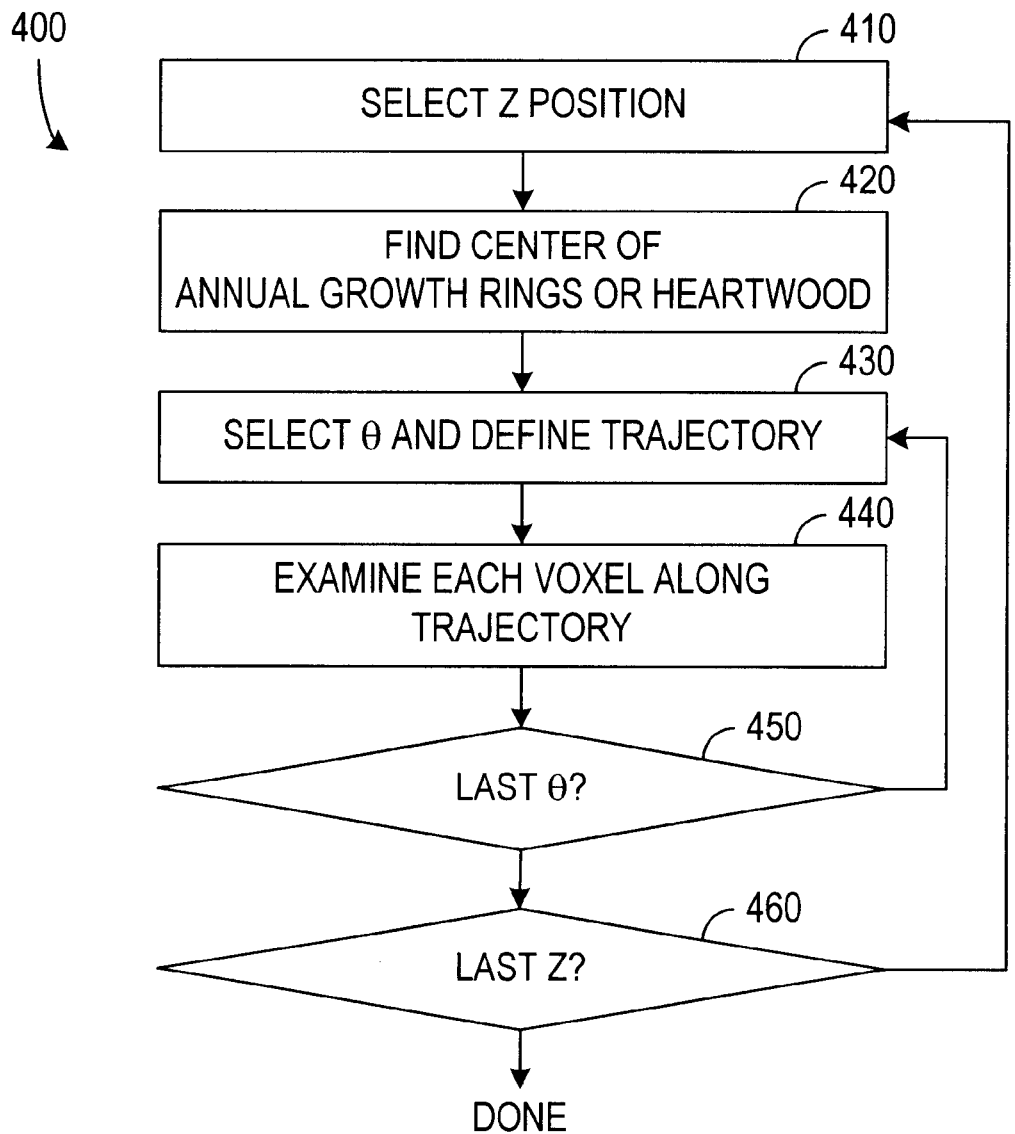
FIG. 4 is a flow diagram of a process employing a modified cylindrical representation to identify the locations of defects in a log.

FIG. 4 is a flow diagram of another process 400 for generating the Z-θ image or two-dimensional data structure in accordance with an embodiment of the invention. For each discrete Z position as selected in a step 410, a step 420 finds the center of the annual growth rings or the geometric center of the log or the heartwood as identified by a density threshold. At each Z position, step 430 selects a value θ identifying a ray or trajectory. The ray goes out at the specified angle θ as projected onto the X-Y plane and up at a limb angle Φ appropriate for the limbs of that log or the species of the tree that provided the log. The evaluated portion of the ray can extend from the center point or be limited to particular distances from the center point. Step 440 examines each voxel along the evaluated portion of the ray and computes a data value based on density, defect severity, distance from center, and previous data values. The determined data value is entered at the given Z,θ position in the image. Steps 450 and 460 respectively loop back to steps 420 and 410 so that the scalar values are determined for all θ and Z positions in the image.

Identification of defects using a threshold or other segmentation techniques based on the absolute magnitude of the density can be difficult because knots and other defects may have the same densities as some of the denser portions of clear wood. Sapwood in softwood species, for example, can be as dense or denser than knots. Also, knots in hardwood species often have a dense exterior with voids of decayed, low-density wood inside. Accordingly, the average density of a knot in hardwood may not indicate the presence of a defect. However, the knowledge that knots originate or extend outward from the center of the growth rings, and upward at an angle specific to the species, simplifies identification of defects. In particular, the ray in a direction characteristic of a knot will maximize the amount of high-density wood traversed and will have an average density higher than rays at angles not aligned with the knot. Similarly, rays that extend along radial cracks have lower average density than do other rays crossing through cracks. The representation in accordance with the invention thus makes defects standout more distinctly among the background of good wood.

As an alternative to picking average densities above or below a threshold to indicate defects, defects can be detected by identifying particular density patterns along a ray. Using rays selected according to the structure of the log (e.g., from the growth center and at an upward angle characteristic of the log) makes the density patterns of defects more consistent and recognizable. For example, voids, or areas of decay inside the log, can be detected by following a ray inward. Starting from the outside of a log, a point along a ray is determined to be inside the log if there is a sufficient distance of wood of a selected density, between the point and the outside of the log. A region of very low density that is found after further movement toward the center indicates a defect.

Observation of variations in the average densities along adjacent rays can also improve ability to distinguish defects from clear wood. In particular, variations in the width of the sapwood region of a log can make the average density for a ray through a thick portion of the sapwood similar to the average density for a ray passing through a small knot and a thin section of sapwood. Accordingly, in this situation, having a fixed threshold average density as the sole indicator of a defect would either miss the small knot or incorrectly identify the region with thick sapwood as a defect region. In accordance with an aspect of the invention, defects can be identified by subtracting a local average from each point in the Z-θ image and then identifying the defects for rays having an average density that differs from a local average density by more that a threshold amount. This provides better discrimination of defects because the thickness of the sapwood changes slowly with both angle θ and distance Z. Accordingly, an area in the Z-θ image having an average density that differs from the average density in a surrounding area of the Z-θ image indicates a defect.

Figure 5:
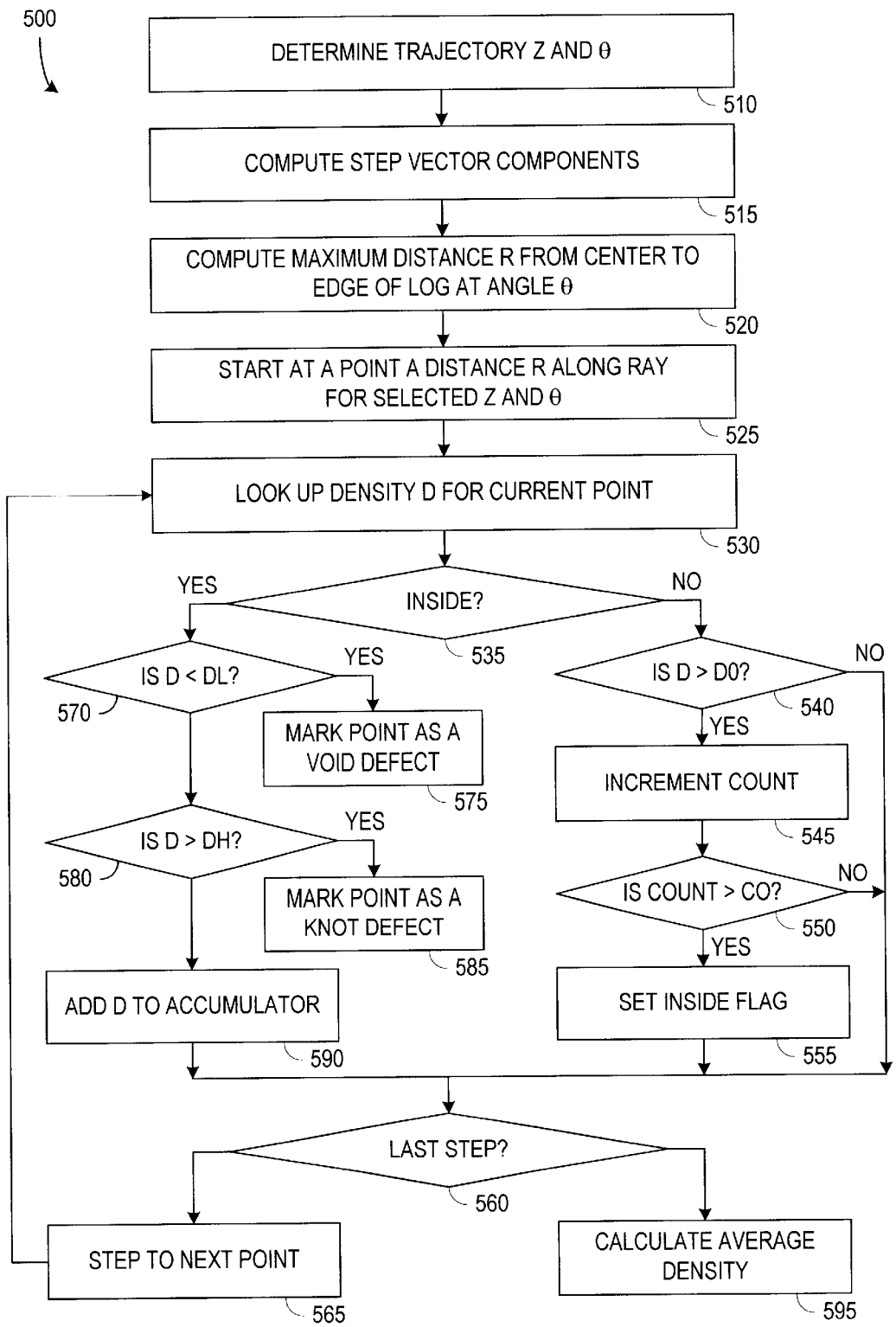
FIG. 5 is a flow diagram of ray tracing process used in creating a defect structure in accordance with an embodiment of the invention.

Once a ray is identified as a defect ray, the depth of the defect can be determined approximately by following the ray inward, moving past the bark and sapwood, until high densities or voids are encountered. FIG. 5 is a flow diagram illustrating a process for tracing a ray and identifying defects along the ray. An initial step 510 selects a trajectory for ray tracing. The trajectory corresponds to constant Z and θ and terminates at the growth center of the log. A limb angle Φ is appropriate to the species being examined. This trajectory has Cartesian coordinates that are a function of the distance from the growth center.

Step 515 determines a step vector having a length S and Cartesian components Sx, Sy, and Sz according to Equations 1.

$Sx = S*\cos(\Phi)*\cos(\theta).$ $Sy = S*\cos(\Phi)*\sin(\theta).$ $Sz = S*\sin((\Phi))$                                            Equation 1:

For each step along the ray, the step vector will be added or subtracted from the Cartesian coordinates a point on the ray to determine the next point for consideration on the ray. An alternative to using fixed limb angle Φ for Sz is a lookup table for limb trajectory. Using a lookup table allows for a curve in the upward growth of the limb (e.g., a changing limb angle). Step 525 selects a starting point that is a distance R along the ray. The distance R can be a fixed value, but in the illustrated process 500, step 520 selects as the distance R the maximum distance from growth center to outside edge of the log at angle θ. Step 530 initializes the Cartesian coordinates of the current point to the point the distance R along the selected ray. Starting at this initial point, process 500 moves inward along the ray in steps of having components Sx, Sy, and Sz, until a specified distance from the growth center is reached.

For each step point along the ray, step 530 finds Cartesian coordinates (Xc,Yc,Zc) of the point and finds the corresponding density D for that point from the three-dimensional data structure representing the log. The use of the density depends on whether process 500 has determined that the current point is "inside" the log. Decision step 535 determines whether the current point is inside the log. The initial or starting point is not inside the log so that process 500 initially branches from step 535 to step 540. Step 540 determines whether the density D is greater than a threshold density D0 characteristic of wood inside a log of the type being analyzed. If in step 540, density D is less than threshold density D0, the current point is outside the log, and process 500 branches from step 540 to step 560 for the next step along the ray. If in step 540, density D is greater threshold density D0, step 545 increments a count of pixels having a density greater than threshold density D0. Then, if in step 550, the count is greater than a threshold count C0, step 555 sets a flag to indicate that process 500 has reached a point inside the log. The threshold count C0 typically depends on the characteristics of the log (e.g., the typical thickness of bark) and the length S of each step.

If the "inside" flag is set, step 535 determines the current pixel is inside the log, and process 500 branches from step 535 to decision step 570, which determines whether density D is less than a low threshold density DL. The low threshold density DL is typically fixed according to the type of wood, but alternative threshold density DL can be selected according to the average densities in surrounding areas of the log. A point that is inside the log and of a low density indicates a void or decay defect, and step 575 marks such points as defects. More particularly, in the two-dimensional defect structure, the data corresponding to the Z and $\theta$ coordinates of the current ray is set to indicate a void type defect and can further include additional information such as the distance along the ray to the defect. After marking the defect in the two-dimensional data structure, tracing process 500 can terminate for the ray.

If density D is not less that the low threshold DL, step 580 determines whether the density is greater than a high threshold density DH. The high threshold density DH is typically fixed according to the type of wood, but alternative threshold density DH can be selected according to the average densities in surrounding areas of the log. If the density D is higher than the high threshold density DH, step 585 updates the two-dimensional data structure to indicate a high-density defect for the pixel corresponding to the ray being traced. If density D is neither higher than DH nor lower than DL, step 590 adds density D to an accumulator.

After step 590, step 560 checks whether the current step is the last step, e.g., tracing has reached a target distance on the ray. If tracing of the ray is not complete, step 565 changes the current coordinates by the amount of the step vector before step 530 looks up a new current density D. If tracing is complete, step 595 divides the accumulator by the number of points detected to form an average density for the ray and sets the appropriate data value in the data structure. The average density can be used in the manners described below to determine whether a defect is present on the ray even when no single voxel on the ray has a density below DL or above DH.

Figure 6:
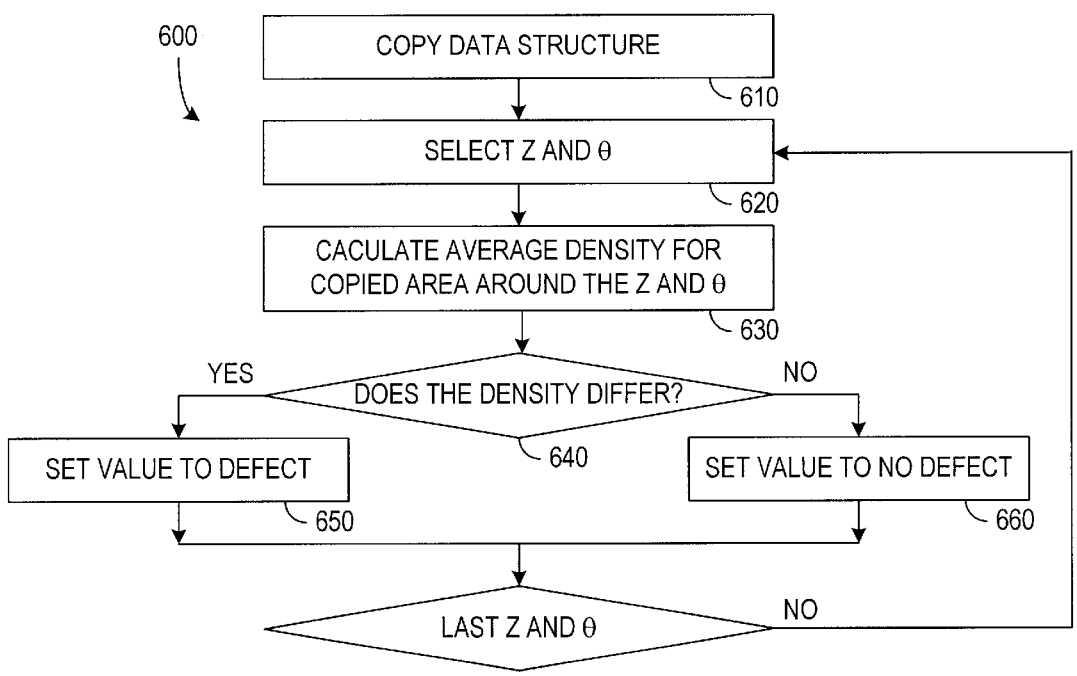
FIG. 6 is a flow diagram of a process of identifying defects that may be hidden by variations in the good wood in a log.

The tracing process 500 can be repeated for each value of Z and $\theta$ in the desired range. The resulting two-dimensional defect structure can be further processed to detect defects that may be hidden by density variations that occur for example, in a log having sapwood that varies in thickness. FIG. 6 illustrates such a process for identifying hidden defects. In process 600, an initial step 610 copies the data structure including average densities for each ray not previously identified as crossing a defect. Step 620 selects values Z and $\theta$ that do not correspond to a previously identified defect, and step 630 calculates an average density from the density values in area (e.g. within 10 degrees and 10 cm) of the selected Z and $\theta$ in the copy. Step 640 determines whether the density for the selected Z and $\theta$ significantly differs from the average density (e.g., a percentage difference greater than about 10% or an absolute difference of about 0.1 or 100 CT counts or Hounsfield units). A significant difference indicates a defect, and step 650 sets the data value corresponding to the selected Z and $\theta$ in the original data structure to indicate the defect. If there is no significant difference, step 660 sets the data value corresponding to the selected Z and $\theta$ in the original defect structure to zero or to otherwise indicate no defect. The resulting defect structure has zero values everywhere except at coordinates corresponding to defects. Such data structures, which are mostly zeros, can be easily compressed for transmission or storage.

Optionally, the defect structures can be further processed. Segmentation for example, can collect groups of adjacent defects into a single defect having a size and shape depending on the defect points collected. Segmentation can also discard isolated defects that are too small to be a problem in the desired application of the log. Further processing can also retrace the rays identified as being defects to find an approximate distance from the center to each defect.

A computer or human can use the Z-$\theta$ defect structure for grading a log. By reducing the data describing the log from three-dimensional to two-dimensional, the data volume is vastly decreased, and the data is easily viewable as an image. Many log grading systems are currently in use or may be developed, but in general, the distribution of defects is of key importance to grading and is typically more important than the total number of defects. The distribution of defects is important because the eventual grade and value of a board is based on the length and width of areas of clear lumber that can be extracted from the board by cutting away the areas containing knots or other defects. A log having several defects aligned along one or two angles $\theta$ can be aligned and cut to provide high value boards that avoid the defects. Accordingly, such logs are of much higher value than a log having the same number of defects at randomly distributed locations. Similarly, if the defects are concentrated at the ends of the log, the log is of higher value because sufficiently long sections of clear wood can found in the middle of the log.

Visual inspection of the Z-$\theta$ defect map quickly indicates the distribution of knots both along the length of the log (Z direction) and angular position $\theta$. An inspector with some training can quickly determine a log's value from the length and width of defect-free sections in the Z-$\theta$ defect map. The alternatives of looking at each CT slice in succession or rotating a three-dimensional rendering are slow and require complex reconstructions and spatial awareness.

An automated grading process can similarly be based on cylindrical projections such as the Z-$\theta$ defect map to produce an objective, quantitative valuation of a log based on a flexible and adaptable set of rules. The rules are modified depending on the species and intended purpose of the log. In particular, a sawyer seeking boards having particular mix of widths, thicknesses, and or lengths can adopt a set of grading rules that grade a log according to the value of boards of the desired mix sawn from the log. The automated grading determines how many sections of the log can produce a defect-free board at least W units wide and L units long. The Z-θ defect map indicates the length and width of clear sections. The angular distance between defects on either side of a clear section in Z-θ defect map and the depth of the wood evaluated (e.g., R2-R1 in FIG. 2) indicate the potential thickness of a -clear board. If a cut is a distance Dc from the center of the log and perpendicular to a radius of the log and the A is the angular distance between the defects, the width of clear wood in the board is about 2*Dc*tan(A/2). The clear length of the board is the Z distance between defects in the Z-θ defect map.

Figure 7A:
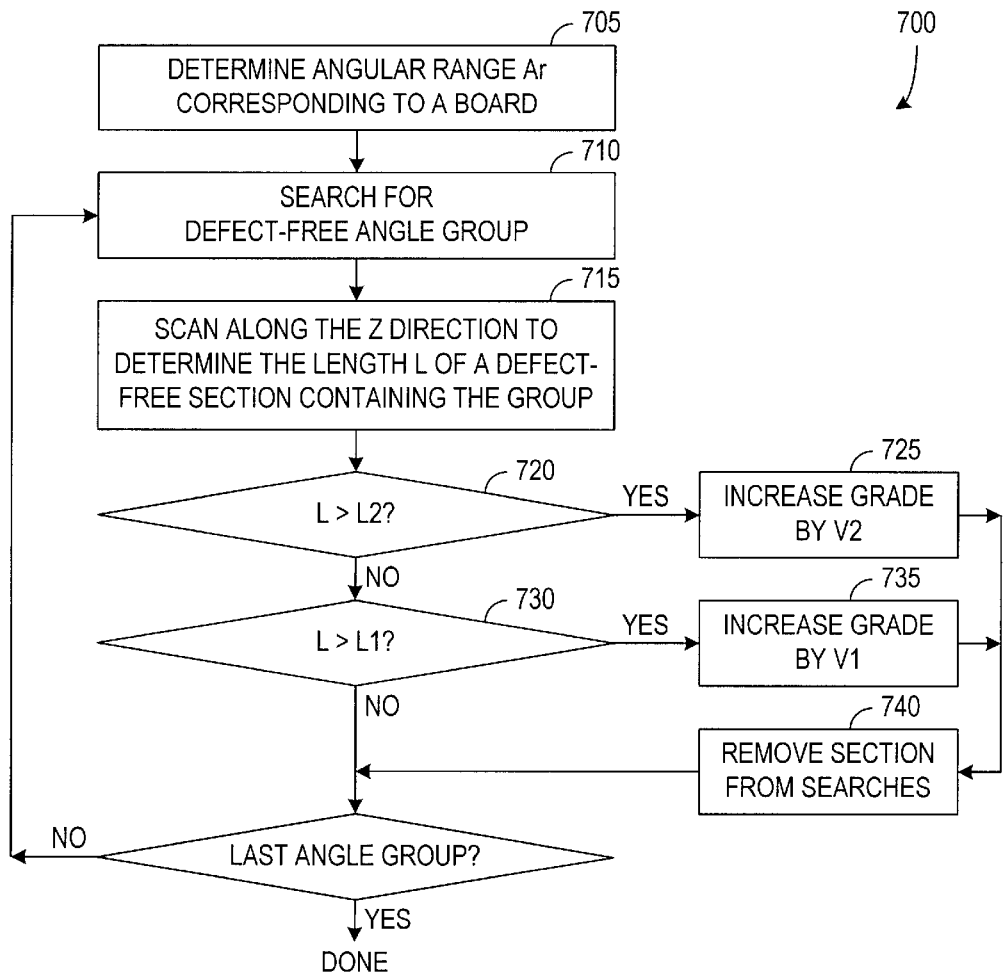
FIGS. 7A and 7B illustrate a log grading process in accordance with and embodiment of the invention.
Figure 7B:
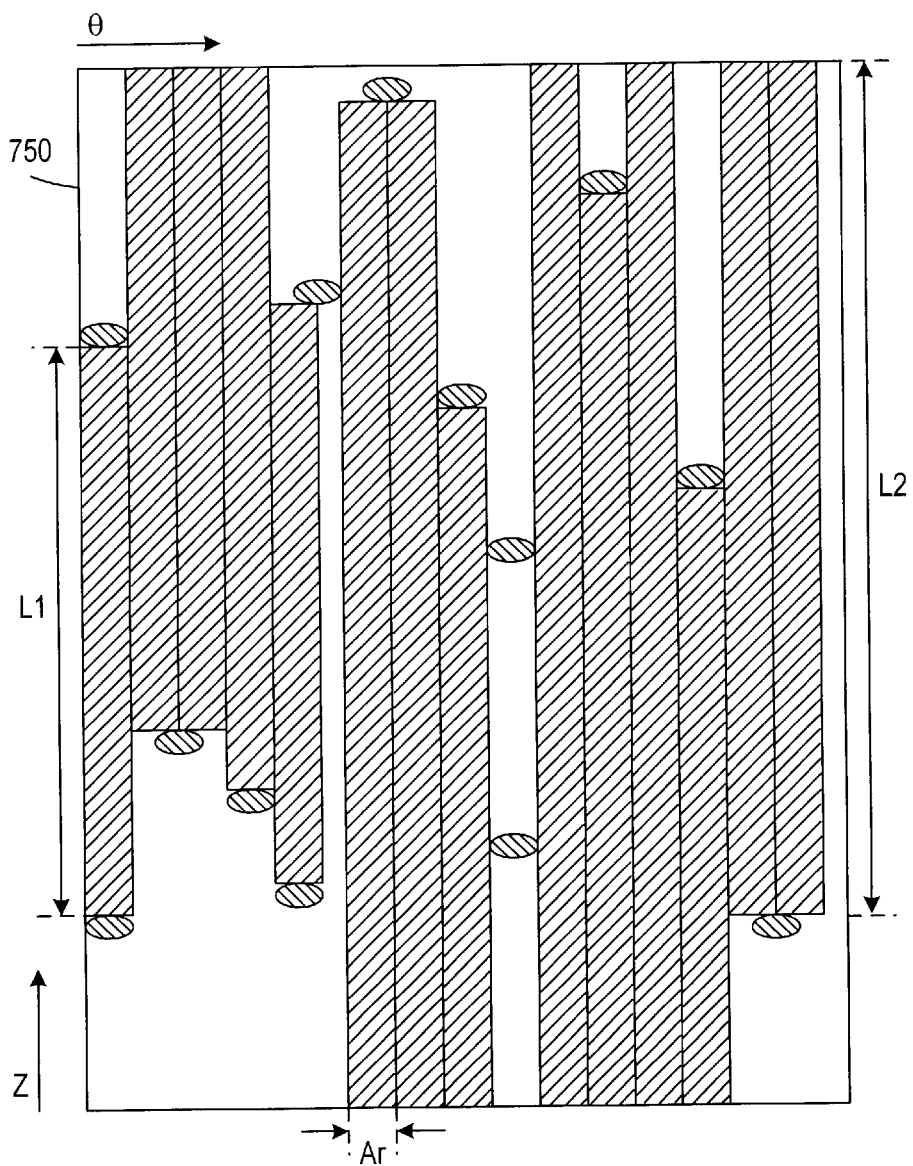
Figure 7B:
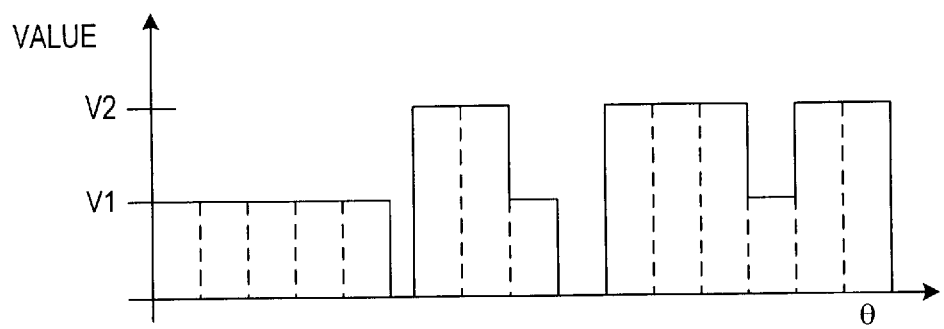

FIGS. 7A and 7B illustrate a grading process 700 of a log based on the number and distribution of defects in a Z-θ defect map 750. In the exemplary process 700 illustrated in FIGS. 7A and 7B, the grading rules select a single width W, and two lengths L1 and L2 for clear sections of board. L2 is longer than L1. Additionally, a clear section having an area greater than or equal to W*L2 is assigned a value V2, and a smaller clear section having an area greater than or equal to W*L1 is assigned a value V1. Alternatively, the assigned value can be a function of the actual length and width of a clear section.

Grading process 700 in an initial step 705 selects an angular distance Ar that produces a board of width W at a cut distance Dc from the center of the log. Process 700 in step 710 searches through Z-θ defect map 750 for a defect-free angle group. A defect-free angle group is a group of A data values that are consecutive in the θ direction (e.g., in a row of the two-dimensional data structure) and indicate no defect. For each defect free angle group found, step 715 of process 700 scans Z-θ defect map 700 in the Z direction (e.g., along columns in the two-dimensional data structure) and finds the length L of a section that is free of defects in all A columns. Alternatively, if the Z-θ defect map 750 contains depth information for defects, the process finds the length of each section having no defects that are greater than the cut distance Dc from the center of the log. If step 720 determines the section associated with an angle group is length L2 or longer, step 725 adds a score V2 to a grade value. Otherwise, if the length L is shorter than L2 and step 730 determines the length L at least as long as length L1, step 735 adds a score V1 to a grade value. Step 740, which follows steps 725 and 735, removes data values in the section from further searching for angle groups so that each defect-free angle group is in at most one section that contributes to the grade value. After completing the searches for defect free angle groups, the total grade value indicates a grade for the log.

The preceding grading process produces an approximate value for a log with no recommended sawing strategy. Efficient sawing of the log might produce a corresponding value for the resulting boards, but a poor sawing job might produce less value. A grading process that accounts for a sawing strategy is inherently more accurate. In particular, a grading process combined with a process to optimize the sawing strategy produces a grade value estimate that more accurately indicates the value of the log.

The sawing strategy can indicate the orientation of a log for each pass through a saw. Frequently, the only freedom provided in a sawing strategy is the orientation of the log during the first cut. Even when a sawing strategy permits additional freedom in selection of cutting parameters, the orientation for the first cut from a log often has the largest affect on the value of the boards produced. Accordingly, the value produced for an optimum initial orientation indicates an optimized grade for a log. In accordance with another aspect of the invention, the Z-θ defect map facilitates optimization of the sawing strategy.

Optimization of the sawing strategy can be done manually based on viewing the image of the Z-θ defect map. In particular, the Z-θ defect image shows the location of the log defects in both Z and θ directions. A person viewing a single Z-θ defect image can select the orientation angle that provides the largest zone of clear wood, or the orientation in which there is the largest area of clear zones. More specifically the first cut can be selected to be perpendicular to the log radius directed at an orientation angle θo that is in the center of the largest clear section in the Z-θ defect image.

Figure 8A:
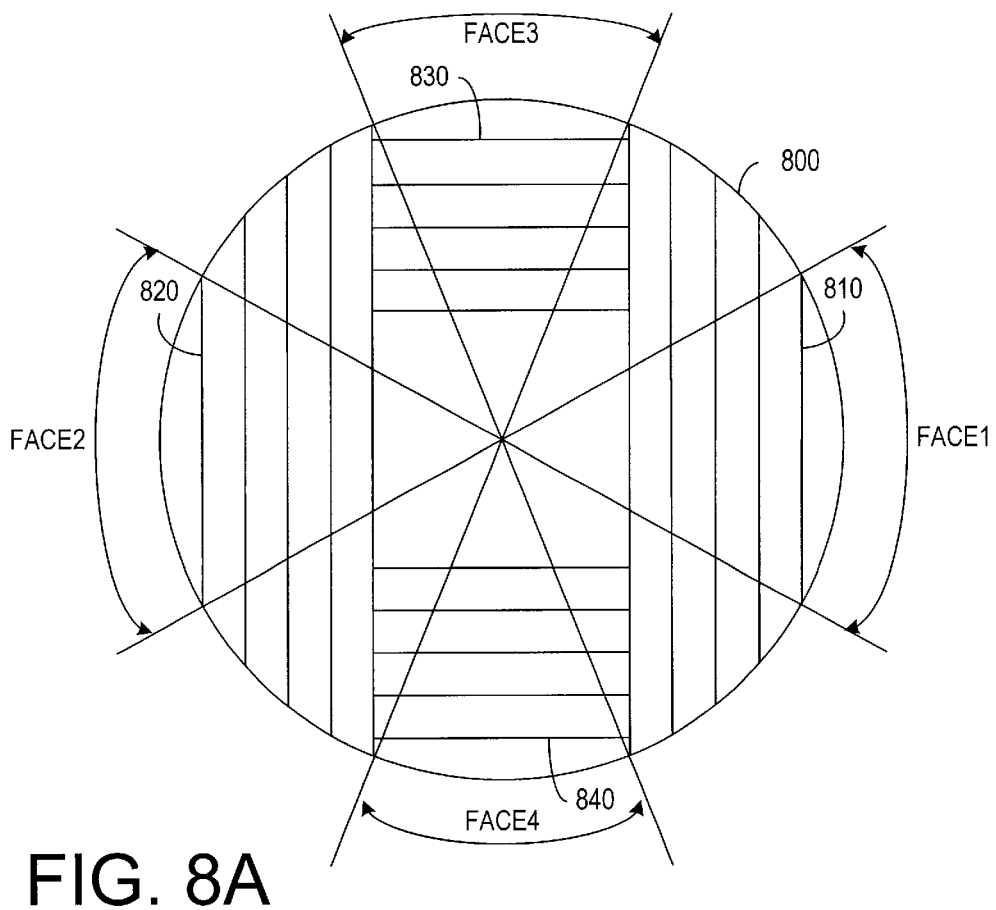
FIGS. 8A and 8B illustrate a sawing strategy and a method in accordance with the invention for optimizing yield of clear wood from a log.

Graphical tools applied to a computerized Z-θ defect image enhance the ability of a person to visualize the range of angles that constitute the boards produced by a sawing strategy. For example, FIG. 8A illustrates an example of a sawing strategy for a log 800. Accordingly to this sawing strategy, a cut 810 at an orientation angle θo opens a first face FACE1 in log 800 A cut 820 at orientation angle θo+180° opens a second face FACE2. A cut 830 at orientation angle θo+90° opens a third face FACE3, and a cut 840 at orientation angle θo+270° opens a fourth face FACE4. Many other sawing strategies are possible, but the strategy of FIG. 8A provides an example for illustration of an aspect of the invention.

Figure 8B:
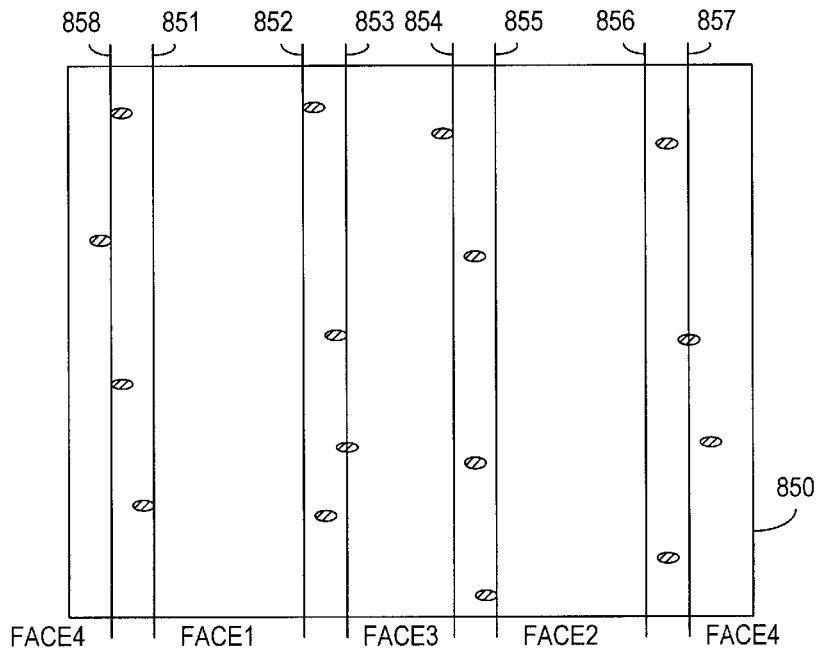

For each face FACE1 to FACE4, each board correspond to a range of angles that depends on the cutting distance Dc and the diameter of log 800. The angular range changes if the cutting distance Dc changes, for example, for subsequent cuts at the same orientation. FIG. 8B illustrates a graphical tool applied to a Z-θ defect image 850 to highlight angular ranges corresponding to boards at each face. The graphics tool adds boundary lines 851 to 858 marking the angular ranges corresponding to each face. Faces FACE1, FACE2, FACE3, and FACE4 correspond to the angular ranges between respective pairs of boundary lines 851 and 852, 853 and 854, 855 and 856, and 857 and 858. A grader or sawyer can shift boundary lines 851 to 858 relative to Z-θ defect image 850 to shift as many defects as possible into unused angular ranges (e.g., between boundary lines 858 and 851, 852 and 853, 854 and 855, or 856 and 857) and provide the largest clear section in the area corresponding to the first face FACE1. Once the boundary lines are shifted to the desired locations, the angle at the center of FACE1 indicates an optimal cutting angle θo.

Figure 9:
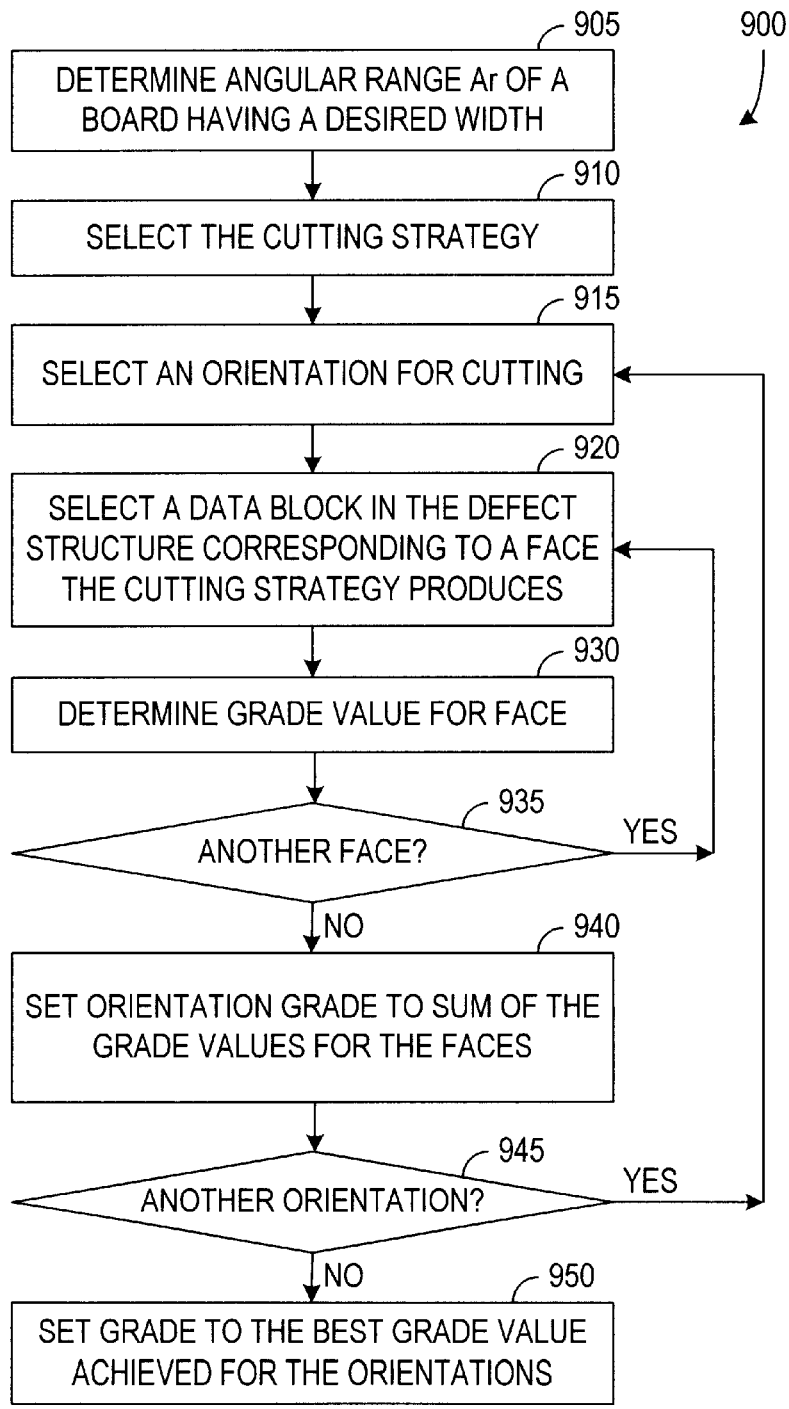
FIG. 9 illustrates a log grading practice that in accordance with an aspect of the invention accounts for a sawing strategy and optimization of log orientation when determining a grade for a log.

The process of optimizing cutting angles based on a cylindrical representation of defects can be automated. The Z-θ defect structure facilitates efficient optimization of sawing orientations by vastly reducing the volume of data processed. FIG. 9 illustrates a grading and optimization process 900 that accounts for the sawing strategy used. An initial step 905 of grading process 900 determines the angular range Ar corresponding to a desired width of clear board. A step 910 then selects the sawing strategy that will be employed on the log, and step 915 selects an initial orientation for the log when the cutting begins. The sawing strategy and the orientation of the log together define the faces that result from cutting the log. Step 920 selects from the defect structure a data block corresponding to a face encounter during the cutting. More specifically, the data block corresponds to an angular range defined by the face selected in step 920. If the defect structure includes depth information, the data block represents defects at the depth corresponding to the face. Step 930 then determines a grade value for the face using, for example, the grading process described above in regard to FIGS. 7A and 7B (but limited to the block corresponding to the selected face.

A loop including selecting a data block for a face (step 920) and determining a grade for the face (step 935) can be repeated for each face defined by the sawing strategy or until step 935 otherwise determines that no further faces need to be considered. Generally, when the defect structure does not contain depth information, not all faces need to be considered. For example, the number of face evaluated can be equal to the number of times that the sawing strategy changes the orientation of the log (e.g., four faces for the cutting strategy of FIG. 8A). Step 940 combines the grade values for the faces evaluated to determine a grade value corresponding to the orientation selected in step 915. In the exemplary embodiment, step 940 sums or averages the grade values for the faces considered.

A loop including steps 915, 920, 935, and 940 repeatedly determines grade values for different orientations of the log until step 945 determines no further orientations need to be considered. Step 950 sets the grade for the log equal to the best grade achieved for any of the orientations. The orientation achieving the highest grade is the recommended initial cut orientation.

Figure 10:
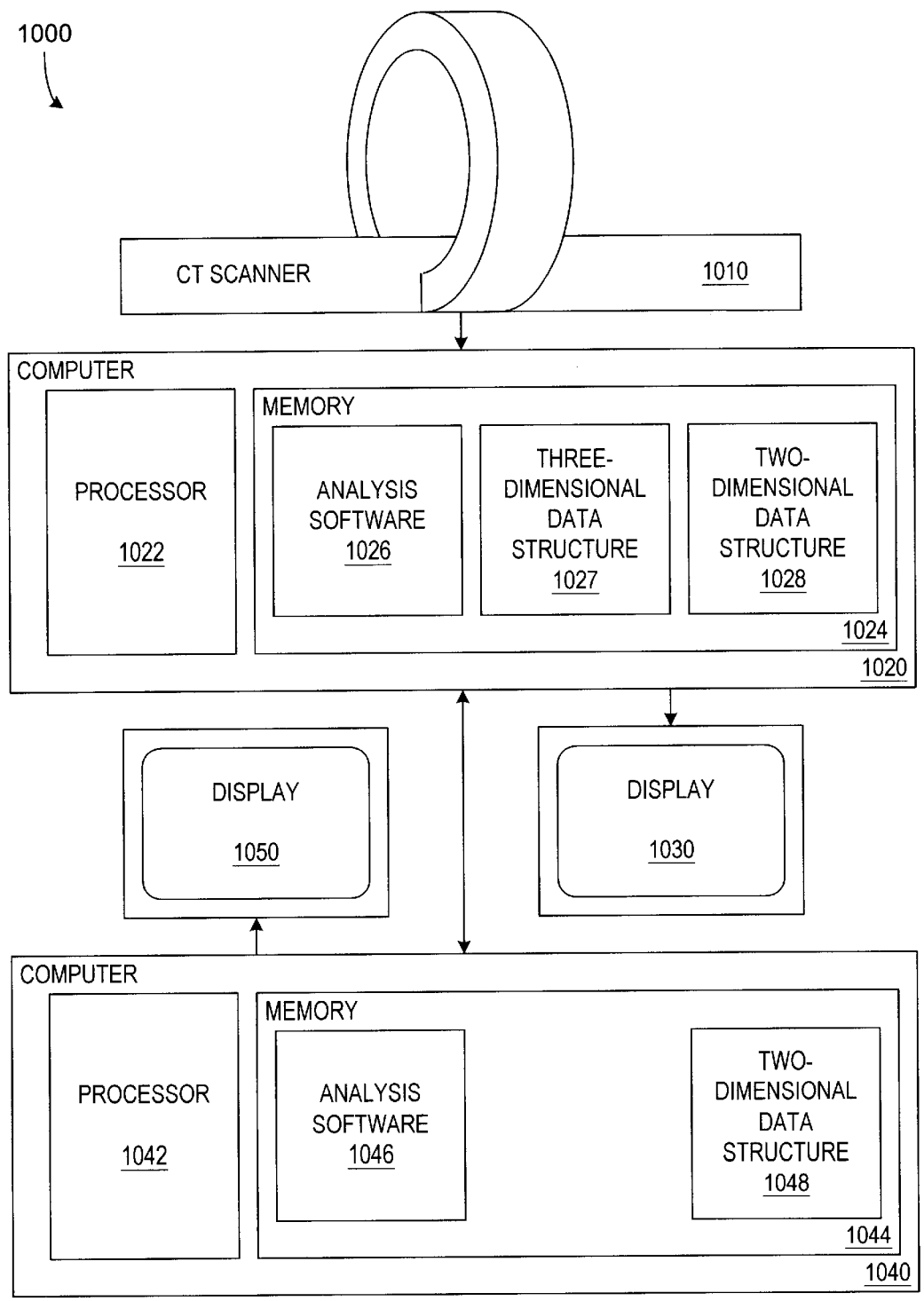
FIG. 10 is a block diagram of a log analysis system in accordance with an embodiment of the invention.

FIG. 10 is a block diagram of a system 1000, which can implement many of the above-described process. System 1000 includes a CT scanner 1010, a computer 1020 with a display 1030, and a computer 1040 with a display 1050. CT scanner 1010 scans a log to produce raw data which conventional CT techniques convert a series of two-dimensional data structures or density distributions corresponding to a series of slices or cross-sections of the log. The collection of all of the two-dimensional data structures together form a three-dimensional data structure 1027. Three-dimensional data structure 1027 can be stored in a memory 1024 of computer 1020 for processing by a processor 1022 executing analysis software 1026. Analysis software 1026 can implement the any of above described automated processes including converting three-dimensional data structure 1027 to a two-dimensional data structure (or defect structure) 1028. A user can view the two-dimensional data structure as an image on display 1030.

Although computer 1020 has access to three-dimensional data structure, such access is not require for analysis of the properties of a log. In particular, computer 1040 has analysis software 1046 that processor 1042 executes analysis software 1046 to process a two-dimensional data structure 1048 in memory 1044. In particular, analysis software 1046 can process data structure 1048 for viewing on display 1050, log grading, or optimizing sawing of a log. Since two dimensional data structure 1028 is much more compact (and is easily compressed) transmission of the two dimensional data structure 1028 to computer 1040 typically takes fewer resources and less time than would transmission of a three dimensional data structure. Accordingly, a user of computer 1040, for example, a log buyer at a sawmill can evaluate a log for a particular sawing strategy or using particular grading criteria without ever needing to deal with the amount of data in the three-dimensional data structure.

Different sawmills with different sawing strategies or different valuations of boards can easily and efficiently evaluate logs based on the sawmills' specific needs.

The Appendix includes listings for subroutines FindPith, FollowPith, BuildRadialView, SegmentRadialimage, and GradeRadialImgage. Subroutine FindPith finds the coordinates of the growth center in a single CT image slice. Subroutine FollowPith finds the growth center in all of the slices of a tree, removes unreliable points, and smoothes the positions. Subroutine BuildRadialView does ray tracing to create a radial image. Subroutine SegmentRadialImage performs local thresholding of the radial image to identify potential defect pixels. Subroutine GradeRadialImgage finds defect free sections in the segmented radial image, selects an optimum opening face, and produces metrics for assigning a grade value to the log.

Although the invention has been described with reference to particular embodiments, the description is only an example of the invention's application and should not be taken as a limitation. Various adaptations and combinations of features of the embodiments disclosed are within the scope of the invention as defined by the following claims.

I claim:

1. A defect structure for a log, comprising:
    a two-dimensional array of data values, the data values corresponding to respective values of a first coordinate Z indicating distance along the log and a second coordinate θ indicating an angle around the log, wherein
    each data value indicates a property of the log that is evaluated along a ray that originates at a center point corresponding to the value of the first coordinate Z for the data value and extends in a direction corresponding to the value of the second coordinate θ for the data value.

2. The defect structure of claim 1, wherein for each value of the first coordinate Z, the center point corresponding to that value of the first coordinate Z is a growth center of the log.

3. The defect structure of claim 2, wherein for each data value, the ray evaluated to determine the data value is directed at an upward angle along the log, the upward angle being characteristic of the log.

4. The defect structure of claim 3, wherein the upward angle is a growth direction of tree limbs and is characteristic of trees of a species that produced the log.

5. The defect structure of claim 1, wherein for each data value, the ray evaluated to determine the data value is directed at an upward angle along the log, the upward angle being characteristic of the log.

6. The defect structure of claim 5, wherein the upward angle is a growth direction of tree limbs and is characteristic of trees of a species that produced the log.

7. The defect structure of claim 1, wherein each data value indicates a property of the log that is only evaluated in a range of distances along the ray that originates at the center point corresponding to the values of the first and second coordinates for the data value.

8. The defect structure of claim 7, wherein the range extends from a first distance from the center point to a second distance from an edge of the log, the first distance excluding core wood from the range, the second distance excluding bark from the range.

9. The defect structure of claim 1, where each data value indicates presence or absence of a defect at a point in the log corresponding to the values of the first and second coordinates for the data value.

10. The defect structure of claim 9, wherein when one of the data values indicates the presence of a defect, the data value also indicates a location of the defect along the ray evaluated for the data value.

11. A method for generating a description of a log, comprising:
    for a set of locations along the length of the log, finding at each location a center point of the log;
    for a set of rays that extend from the center points, evaluating a property of the log along each ray to generate a data value corresponding to a value of a first coordinate Z identifying the location for the ray and a value of a second coordinate θ identifying a direction of the ray; and constructing a two-dimensional data structure that describes the log, the two dimensional data structure including the data values at positions in the two-dimensional data structure according to the respective values of the first and second coordinates.

12. The method of claim 11, wherein finding the center point for one of the locations comprises finding a center of annual growth rings in the log at the location.

13. The method of claim 11, wherein evaluating the property of the log along one of the rays comprises evaluating density of the log along the ray to determine whether there is a defect along the ray, in the log.

14. The method of claim 13, further comprising performing CT scanning of the log to generate a three-dimensional data structure that provides the densities evaluated along the rays.

15. A system for evaluating a log, comprising a program code that is computer executable for manipulating a data structure for the log, wherein the data structure comprises:

a two-dimensional array of data values, the data values corresponding to respective values of a first coordinate Z indicating distance along the log and a second coordinate θ indicating an angle around the log, wherein each data value indicates a property of the log that is evaluated along a ray that originates at a center point corresponding to the value of the first coordinate Z for the data value and extends in a direction corresponding to the value of the second coordinate θ for the data value.

16. The system of claim 15, further comprising:

a display device; and a processor capable of executing the program code, wherein in executing the program code the processor controls display of an image on the display device, the image including pixels that correspond to the data values of the data structure and have shades defined by the respective data values.

17. The system of claim 16, wherein executing the program code further superimposes marks in the image, the marks indicating boundaries of one or more faces of the log that results when sawing the log.

18. The system of claim 17, wherein executing the program code further permits user controlled shifting of the marks relative to the image.

19. The system of claim 15, wherein the program code manipulates the data structure to generate a grade value for the log.

20. A method for grading a log, comprising:

determining a computer tomography (CT) data structure representing the log; and processing the CT data structure to arrive at a grade for the log, wherein processing the CT data comprises:

creating a two-dimensional array of data values indicating a defect structure of the log, each data value indicating presence or absence of a defect in a portion of the log corresponding to the data value, wherein each data value in the two dimensional array corresponds to values of a first coordinate Z indicating a position along the length of the log and a second coordinate θ indicating an angle around the log;

evaluating the two-dimensional array to determine sizes of blocks in the two-dimensional array, that are free of data values indicating defects; and assigning the grade to the log according to the sizes.

21. The method of claim 20, wherein evaluating the two-dimensional array comprises:

creating an image having pixels that correspond to the data values and have shades according to the data values; and viewing of the image by a grader, wherein the grader recognizes the sizes of the blocks through evaluating areas of the image having a shade indicating an absence of defects.

22. The method of claim 21, wherein the grader assigns the grade to the log qualitatively based on the viewing of the image.

23. The method of claim 21, further comprising superimposing on the image, marks indicating boundaries of one or more faces of the log that results from a sawing strategy for the log.

24. The method of claim 23, further comprising shifting the image relative to the marks to minimizes defects within the boundaries of the one or more faces.

25. The method of claim 24, further comprising selecting an orientation of the log according to positions of the marks that minimize defects within the boundaries of the one or more faces.

26. The method of claim 20, wherein evaluating the two-dimensional array comprises executing a computer program that manipulates the two-dimensional array.

27. The method of claim 26, wherein executing the computer program comprises:

(a) determining a number N of data values that are consecutive in a direction of the second coordinate θ and correspond to a desired width of defect-free wood;

(b) scanning the two-dimensional array in the direction of the second coordinate until identifying N consecutive data values that indicate absence of a defect;

(c) scanning the two-dimensional array in a direction of the first coordinate to determine a size of a block that is defect free;

(d) increasing the grade value for the log by an amount corresponding to the size of the block that is defect-free;

(e) repeating steps b, c, and d to account for defect-free blocks in the two-dimensional data structure.

28. A method for grading a log comprising:

(a) creating a two-dimensional array of data values indicating a defect structure of the log, each data value indicating presence or absence of a defect in a portion of the log corresponding to the data value, wherein data values in the two dimensional array correspond to values of a fist coordinate Z indicating a position along the length of the log and a second coordinate θ indicating an angle around the log;

(b) selecting a sawing strategy for the log;

(c) selecting an orientation of the log for the sawing strategy;

(d) identifying a sub-array of the two-dimensional array, the sub-array corresponding to a face of the log resulting from the sawing strategy and the orientation;

(e) evaluating the sub-array to determine sizes of blocks in the sub-array, that are free of data values indicating defects; and (f) assigning a first grade value to the face according to the sizes;

(g) repeating steps (d), (e), and (f) for one or more faces of the log resulting from the sawing strategy and the orientation;

(h) combining the first grade values of the faces to generate a second grade value for the orientation; and (i) repeating steps (c) to (h) for one or more additional orientations of the log;

(j) assigning a third grade value to the log based on a best of the second grade values.

29. A method for identifying a growth center of a log, comprising:

for each line in a first set of lines through a cross-section of the log, determining an accumulated absolute value of a gradient of density of the log along the line;

identifying a first line that is in the first set and has an accumulated absolute value as large as any determined for lines in the first set;

for each line in a second set of lines through the cross-section of the log, determining an accumulated absolute value of a gradient of density of the log along the line;

identifying a second line that is in the second set and has an accumulated absolute value as large as any determined for lines in the second set; and identifying the growth center as being at an intersection of the first line and the second line.

30. The method of claim 29, wherein the lines in the first set are perpendicular to the lines in the second set.

31. The method of claim 29, further comprising:

determining a geometric center of the log; and selecting a central area that is smaller than the cross-section of the log and contains the geometric center of the log, wherein each line in the first and second sets passes through the central area.

32. The method of claim 31, wherein determining the accumulated absolute values of the gradient of the density of the log only considers densities for points inside the central area.

* * * * *